(12) United States Patent
Guarracino et al.

(10) Patent No.: US 6,225,524 B1
(45) Date of Patent: May 1, 2001

(54) ABSORBENT ARTICLES HAVING AN ODOR CONTROL SYSTEM CONSISTING OF ABSORBENT GELLING MATERIAL AND SILICA

(75) Inventors: Mario Guarracino, Silvi Marina; Alessandro Gagliardini, Jesi, both of (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/194,961

(22) PCT Filed: May 23, 1997

(86) PCT No.: PCT/US97/08965

§ 371 Date: Dec. 7, 1998

§ 102(e) Date: Dec. 7, 1998

(87) PCT Pub. No.: WO97/46189

PCT Pub. Date: Dec. 11, 1997

(30) Foreign Application Priority Data

Jun. 7, 1996 (EP) .................................................. 96109177

(51) Int. Cl.$^7$ .............................. A61F 13/15; A61F 13/20
(52) U.S. Cl. .......................... 604/359; 604/367; 604/358; 604/385.01
(58) Field of Search ................................... 604/358, 367, 604/375, 359, 385.01

(56) References Cited

U.S. PATENT DOCUMENTS

| | | | |
|---|---|---|---|
| 5,306,487 | * | 4/1994 | Karapasha et al. .................. 424/76.6 |
| 5,407,442 | * | 4/1995 | Karapasha ............................ 604/359 |

* cited by examiner

Primary Examiner—Glenn K. Dawson
Assistant Examiner—Michele Kidwell
(74) Attorney, Agent, or Firm—Theodore P. Cummings; Matthew P. Fitzpatrick; Kevin C. Johnson

(57) ABSTRACT

The present invention relates to an absorbent article in particular sanitary napkins and panty liners, comprising a liquid permeable topsheet, a backsheet and an absorbent core intermediate the topsheet and backsheet. The absorbent article further comprises an improved odor control system comprising the combination of absorbent gelling material with silica.

6 Claims, No Drawings

ABSORBENT ARTICLES HAVING AN ODOR CONTROL SYSTEM CONSISTING OF ABSORBENT GELLING MATERIAL AND SILICA

FIELD OF THE INVENTION

The present invention relates to absorbent articles, in particular sanitary napkins and panty liners comprising compositions providing odour control benefits.

BACKGROUND OF THE INVENTION

Whilst the primary focus of absorbent articles remains the ability of these articles to absorb and retain fluids, another important area of development in this field is the control of odourous compounds contained within the absorbed fluids or their degradation products. There are a wide range of compounds which may be present in an absorbent article during use which result in the formation of malodourous. These compounds include fatty acids, ammonia, amines, sulphur containing compounds and ketones and aldehydes.

The art is replete with descriptions of various odour controlling agents for use in absorbent articles in order to address the problem of malodour formation. These agents can typically be classified according to the type of odour the agent is intended to combat. Odours may be classified as being acidic, basic or neutral. Acidic odour controlling agents have a pH greater than 7 and typically include inorganic carbonates, bicarbonates, phosphates and sulphates. Basic odour controlling agents have a pH of less than 7 and include compounds such as citric acid, boric acid and maleic acid.

Neutral odour controlling agents have a pH of approximately 7. Examples of these types of compounds include activated carbons, clays, zeolites, silicas and starches. Such neutral odour controlling agents are the most commonly utilised in absorbent articles.

For example EPO 348 978 discloses an absorbent article comprising an odour control system wherein the neutral odour controlling particles are selected from carbon, clays, silicas, zeolites and molecular sieves. EPO 510 619 relates to absorbent article comprising odour control complex including a combination of at least 2 agents selected form a group which includes zeolites and silica gels. Similarly, WO 91/12029, WO 91/11977 and WO 91/12030 disclose the combination of zeolites and absorbent gelling materials.

EPO 282 287 discloses a deodouriser suitable for use in a sanitary napkin which is non black comprising at least one compound selected from metal silicates and metal salts of aluminum containing silicates selected from certain transition metals and group II metals.

WO 81/01643 relates to the removal of nitrogenous irritants present in waste matter in diapers by the use of an inorganic aluminosilicate zeolite ammonium ion exchange material. In addition silica gel may be present to absorb additional water. Carbon is a preferred component of the system Carbon has been noted in the art as being particularly effective over a broad spectrum of odours. However, it is not favoured due to its black appearance, which is considered unacceptable by consumers. Hence a currently preferred odour control agent is zeolite particularly the so-called intermediate and high ratio zeolites. Although zeolite does not have a negative aesthetic profile, its main drawback is its lack of effective odour control over a broad range of odour types and the expense of such materials.

Consequently, there still exists a need to provide an odour controlling agent or system which has an acceptable aesthetic profile such that it is light coloured and provides effective odour control over a wide range of malodourous compounds and which is not expensive.

It has now been observed that this need may be addressed by the use of the combination of zeolite with silica to effectively combat a wide range of odours which may be present within an absorbent article. Furthermore, the wide range odour control benefits are provided by a dual component system not a tri component system.

An additional advantage of the present invention is that the odour control system comprises components which are all light in colour and thus are not noticeable within the absorbent article and are therefore acceptable from a consumer standpoint.

None of the identified prior art has recognised that this specific combination of absorbent gelling materials and silica provides the above described benefits.

SUMMARY OF THE INVENTION

The present invention relates to an absorbent article comprising a liquid pervious topsheet, a backsheet and an absorbent core intermediate said topsheet and said backsheet, characterised in that said absorbent article comprises an odour control system comprising the combination of silica or a metal silicate excluding transition metals having a molecular weight of 136 or more with absorbent gelling material.

DETAILED DESCRIPTION OF THE INVENTION

The present invention relates to absorbent disposable articles such as sanitary napkins, baby diapers, incontinence products and panty liners. The absorbent article of the present invention comprise the essential features of a liquid pervious topsheet a backsheet and an absorbent core intermediate the topsheet and the backsheet. The absorbent article further comprises as an essential component an odour control system.

Odour Control System

According to the present invention the absorbent article comprises as an essential feature an odour control system comprising the combination of an absorbent gelling material and silica, which is effective over a wide range of malodours.

Absorbent Gelling Materials

Thus according to the present invention the odour controlling system comprises as an essential component absorbent gelling material. As is well-known from recent commercial practice, absorbent gelling materials (sometimes referred to as "super-sorbers") are becoming broadly used in absorbent articles. AGM's are materials which have fluid-absorbing properties. Such materials form hydrogels on contact with water (e.g., with urine, blood, and the like). One highly preferred type of hydrogel-forming, absorbent gelling material is based on polyacids, especially polyacrylic acid. Hydrogel-forming polymeric materials of this type are those which, upon contact with fluids (i.e., liquids) such as water or body fluids, imbibe such fluids and thereby form hydrogels. These preferred absorbent gelling materials will generally comprise substantially water-insoluble, slightly cross-linked, partially neutralized, hydrogel-forming polymer materials prepared from polymerizable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, the preferred absorbent gelling materials include hydrolyzed acrylonitrile grafted starch, acrylic acid grafted starch, polyacrylates, maleic anhydride-based copolymers and combinations thereof. Especially preferred absorbent gelling materials are the polyacrylates and acrylic acid grafted starch.

Whatever the nature of the polymer components of the preferred absorbent gelling materials, such materials will in general be slightly cross-linked. Crosslinking serves to render these preferred hydrogel-forming absorbent materials substantially water-insoluble, and cross-linking also in part determines the gel volume and extractable polymer characteristics of the hydrogels formed therefrom. Suitable cross-linking agents are well known in the art and include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer materials; and (4) polyvalent metal compounds which can from ionic cross-linkages. Cross-linking agents of the foregoing types are described in greater detail in Masuda et al; U.S. Pat. No. 4,076,663; Issued Feb. 28, 1978. Preferred cross-linking agents are the di- or polyesters of unsaturated mono-or polycarboxylic acids with polyols, the bisacrylamides and the di-or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the gelling materials used herein.

The preferred, slightly cross-linked, hydrogel-forming absorbent gelling materials will generally be employed in their partially neutralized form. For purposes described herein, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to as the "degree of neutralization". Typically, commercial absorbent gelling materials have a degree of neutralization somewhat less than 90%.

The preferred absorbent gelling materials used herein are those which have a relatively high capacity for imbibing fluids encountered in the absorbent articles; this capacity can be quantified by referencing the "gel volume" of said absorbent gelling materials. Gel volume can be defined in terms of the amount of synthetic urine absorbed by any given absorbent gelling agent buffer and is specified as grams of synthetic urine per gram of gelling agent.

Gel volume in synthetic urine (see Brandt, et al, below) can be determined by forming a suspension of about 0.1–0.2 parts of dried absorbent gelling material to be tested with about 20 parts of synthetic urine. This suspension is maintained at ambient temperature under gentle stirring for about 1 hour so that swelling equilibrium is attained. The gel volume (grams of synthetic urine per gram of absorbent gelling material) is then calculated from the weight fraction of the gelling agent in the suspension and the ratio of the liquid volume excluded from the formed hydrogel to the total volume of the suspension. The preferred absorbent gelling materials useful in this invention will have a gel volume of from about 20 to 70 grams, more preferably from about 30 to 60 grams, of synthetic urine per gram of absorbent gelling material.

Another feature of the most highly preferred absorbent gelling materials relates to the level of extractable polymer material present in said materials. Extractable polymer levels can be determined by contacting a sample of preferred absorbent gelling material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issues Mar. 31, 1987, Reissue 32,649, The absorbent gelling materials which are especially useful in the absorbent articles herein are those which have an equilibrium extractables content in synthetic urine of no more than about 17%, preferably no more than about 10% by weight of the absorbent gelling material.

The absorbent gelling materials herein before described are typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

The size of the absorbent gelling material particles may vary over a wide range. For reason of industrial hygiene, average particle sizes smaller than about 30 microns are less desirable. Particles having a smallest dimension larger than about 2 mm may also cause a feeling of grittyness in the absorbent article, which is undesirable from a consumer aesthetics standpoint. Furthermore, rate of fluid absorption can be affected by particle size. Larger particles have very much reduced rates of absorption. Preferred for use herein are absorbent gelling material s particles substantially all of which have a particle size of from about 30 microns to about 2 mm. "Particle Size as used herein means the weighted average of the smallest dimension of the individual particles.

The amount of absorbent gelling material particles used in absorbent articles will typically range from 20 $gm^{-2}$ to 150 $gm^{-2}$, preferably from 40 $gm^{-2}$ to 110 $gm^{-2}$, more preferably from 55 $gm^{-2}$ to 85 $gm^{-2}$.

Silica Odour Control Agent

According to the present invention the odour control system comprises as an essential component silica. Silica i.e. silicon dioxide $SiO_2$ exists in a variety of crystalline forms and amorphous modifications, and can be derived from both natural sources e.g. diatomaceous earth and synthetic sources, any of which are suitable for use herein. In particular, silicas having a high surface area or in agglomerated form are preferred. Preferably the silica is in a highly purified form such that is contains at least 90%, preferably 95%, more preferably 99% silicon dioxide. Most preferably the silica is silica gel having a 100% silica content. Alternatively the silica may be provided from other sources such as metal silicates including sodium silicate. However, metal silicates from transition metals having a molecular weight of 136 or more are excluded.

Preferred silica include non crystalline silica (e.g. amorphous silica, appearing as white free flowing powder), having a particle size 4–12 microns, a pore volume 1–2 g/ml or a granular silica of aggregated particles (e.g. silica gel, having a maximum particle dimensions of 1.6 mm in diameter). More preferred is silica gel having a medium pore diameter of from 40 Å to 150 Å, preferably from 60 Å to 130 Å, most preferably from 90 Å to 110 Å, a surface area of from 100 m2/g to 800 m2/g, preferably from 200 m2/g to 550 m2/g, most preferably from 250 m2/g to 350 m2/g and an average particle size of 15 to 200 microns, preferably from 63 to 200 microns.

The absorbent article preferably comprises from 40 $gm^{-2}$ to 100 $gm^{-2}$, more preferably from 60 $gm^{-2}$ to 90 $gm^{-2}$, most preferably from 60 $gm^{-2}$ to 65 $gm^{-2}$ of silica based on 100% purity.

According to the present invention the weight of the odour control system which may be used in the absorbent article can be readily determined by the skilled person bearing in mind the absorbent article dimensions. For example, when utilised in a sanitary napkin or panty liner, the absorbent article may comprise from 0.5 g to 5 g, preferably from 1 g to 3 g, most preferably from 1.5 g to 2.5 g of said odour control system.

The ratio of the absorbent gelling material to silica is from 1:5 to 1:1, preferably from 1:3: to 1:1, most preferably from 1:1.5 to 1:1.

According to the present invention the odour control system may comprise additional optional components such as antimicrobial agents, perfuming ingredients, masking agents, activated carbon, zeolites and chelants, all of which are known to the those skilled in the art.

The odour control system may be incorporated into the absorbent article by any of the methods disclosed in the art, for example layered on the core of the absorbent article or mixed within the fibres of the absorbent core. The odour control system is preferably incorporated between two layers of cellulose tissue. Optionally the system may be bonded between two cellulose tissue layers with, for example, a hot melt adhesive or any suitable bonding system.

More preferably the odour control system is incorporated in a layered structure in accordance with the disclosure of WO 94/01069 or Italian patent application number TO 93A 001028. TO 93A 001028 describes a layered structure substantially as described in WO 94/01069 with the exception that TO 93A 001028 comprises a much higher quantity of absorbent gelling material in the intermediate layer which is between the fibrous layers (120 $gm^{-2}$) that would be incorporated as an optional component in the present invention. The intermediate layer comprises in particular a polyethylene powder as thermoplastic material which is mixed with the premixed odour control system of the present invention. The mixture is then heated such that the polyethylene melts and glues the laminate layers and components together. The bridges which form the bond points between the fibrous layers involve particles of AGM as well as particles of thermoplastic material. (The absorbent capacity of the AGM is unaffected by bonding.) The adhesive lines are preferably also placed on the edges of the laminate to ensure that the edges of the laminate stick and any loose odour control material does not fall out of the laminate.

Absorbent Core

According to the present invention, the absorbent core can include the following components: (a) an optional primary fluid distribution layer preferably together with a secondary optional fluid distribution layer; (b) a fluid storage layer; (c) an optional fibrous ("dusting") layer underlying the storage layer; and (d) other optional components. According to the present invention the absorbent core may have any thickness depending on the end use envisioned.

a Primary/Secondary Fluid Distribution Layer

One optional component of the absorbent core according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilised. The fluid distribution layers can be comprised of any material typical for such distribution layers. In particular fibrous layers maintain the capillaries between fibers even when wet are useful as distribution layers.

b Fluid Storage Layer

Positioned in fluid communication with, and typically underlying the primary or secondary distribution layers, is a fluid storage layer. The fluid storage layer can comprise any usual absorbent material or combinations thereof. It preferably comprises absorbent gelling materials in combination with suitable carriers.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins and panty liners.

An embodiment of the absorbent structure made according to the present invention may comprise multiple layers comprises a double layer tissue laminate formed by folding the tissue onto itself. These layers can be joined to each other for example by adhesive or by mechanical interlocking or by hydrogen bridge bands. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

The Topsheet

According to the present invention the absorbent article comprises as an essential component a topsheet The topsheet may comprise a single layer or a multiplicity of layers. In a preferred embodiment the topsheet comprises a first layer which provides the user facing surface of the topsheet and a second layer between the first layer and the absorbent structure/core.

The topsheet as a whole and hence each layer individually needs to be compliant, soft feeling, and non-irritating to the wearer's skin. It also can have elastic characteristics allowing it to be stretched in one or two directions. According to the present invention the topsheet may be formed from any of the materials available for this purpose and known in the art, such as woven and non woven fabrics and films. In a preferred embodiment of the present invention at least one of the layers, preferably the upper layer, of the topsheet comprises a hydrophobic, liquid permeable apertured polymeric film. Preferably, the upper layer is provided by a film material having apertures which are provided to facilitate liquid transport from the wearer facing surface towards the absorbent structure. If present the lower layer preferably comprises a non woven layer, an apertured formed film or an airlaid tissue.

Backsheet

According to the present invention the absorbent article comprises as an essential component a backsheet. The backsheet primarily prevents the extrudes absorbed and contained in the absorbent structure from wetting articles that contact the absorbent product such as underpants, pants, pyjamas and undergarments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

The backsheet typically extends across the whole of the absorbent structure and can extend into and form part of or all of the preferred sideflaps, side wrapping elements or wings.

The backsheet can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matt finished to provide a more clothlike appearance. Further, the backsheet can permit vapours to escape from the absorbent structure, i.e. be breathable, while still preventing extrudates from passing through the backsheet. Also breathable backsheets comprising several layers, e.g. film plus non-woven structures, can be used.

EXAMPLES

The sanitary napkins used in the following examples were Always (Always is a registered Trade Mark) as sold by the Procter & Gamble Company. Each napkin was opened by cutting the wrap around the perforated coverstock at its bottom face approximately along a longitudinal edge of the release paper which covers the external adhesive layer. The side of the absorbent fibrous core is then exposed by slightly shifting the water impermeable plastic bottom layer and subsequently, the fibrous core is split into two halves, each having approximately the same thickness, along a plane which is parallel to the plane of the napkin itself. The odour control system is homogeneously distributed between these tow fibrous layers which are then joined together to reconstitute the absorbent core.

The water impermeable inner backsheet is then put back into its original position and the wrap around perforated coverstock is sealed along the cut by means of a e.g. a double sided adhesive tape.

Samples were produced using the method above, containing the odour control systems as described hereinbelow. A commercially available Always sanitary napkin containing no AGM and otherwise without modification was used as a reference.

The absorbent gelling material used was XZ 9589001, available from Dow Chemicals. The silica used was Silica gel code 40,360-1, available from Merck.

Odour Control Test

Principle of the Test in vivo sniff test consists of providing the test products to the users, wearing the products and returning them for analysis by expert graders that express their judgment about the (Un)pleasantness of the odour of the pad.

Each test comprises five separate stages:
1. Consignment of products
2. Wearing of products
3. Product return and preparation of test samples
4. Sniff test
5. Statistical analysis of the data

Consignment of the Product

Women are chosen who are known to have an odour control problem. Each of five women selected were given one product per test sample individually packed in an anonymous bag.

Wearing of the Products

Each woman wears the products in an alternating way. For example: if the first woman wears the product A, then product B and then the product C, the second woman wears the products in order B, C, A and so on. This is to ensure that the products are worn under the same conditions. The products are worn for as per habit and are frozen (at least at −20° C.) immediately after removal.

Product Return and Preparation of the Test Samples

The products are collected every day and are kept frozen (−60° C.) until all the used products from the same women have been collected. The used pads are thawed to room temperature for 2/3 hours before testing. The products are then weighed to estimate the loading of menstrual fluid. Among the products, one reference pad which has not been worn is added. The used products are then placed into an aluminium tray covered with a perforated aluminium sheet.

Sniff Test

Sniff test session takes place in a large air-conditioned room with relatively rapid air turnover and is performed by at least six graders who have to sniff all the products of the same woman in each sniff test session. The grader may use any convenient sniffing strategy during this time, but is asked to be consistent throughout the test. During a test, graders sniff on the perforated aluminium sheet for approximately 5 seconds; the graders sniffs products at several seconds intervals from each them. In these conditions every sniffer evaluates the odour of each series of products using a (Un)pleasantness scale which ranges from −10 (highest level of unpleasantness) to 5 (most pleasant). With this procedure, each grader compares MU (Unpleasantness) in the test session. The relative MU odour values from different products are assigned numbers. For example, in a test session, a sample that is perceived to be twice as strong as another is assigned twice as large a number. One that is perceived to be one-tenth as strong as another is assigned a number one-tenth as large, etc. In each test session, zero is used to designate neutral hedonicity, and + and − numbers are assigned in ratio proportion to the relative pleasantness and unpleasantness of the odour.

The Unpleasantness values, for each sample, is obtained as a mean of at least 72 observations (six women, two products each, six graders).

Statistical Analysis of the Data

The results collected from the test is then analysed by statistical analysis software (SAS). The data is processed to show statistically significant differences among untreated and treated products. The difference is shown in the tables by means of a letter near every mean value. Results with the same letter are not statistically significantly different. Duncan's multiple range test is used to form multiple comparisons.

Results

Using the above method values of the (Un)pleasantness of the odour (MU) are obtained. Generally MU values are negative i.e. the higher the negativity the stronger the unpleasantness of the odour. The MU value gives an indication of the effectiveness of an odour control system. As can be seen from the results, the combination of silica and AGM provides a significantly improved odour control performance.

| Product | Ref | 1 | 2 |
|---|---|---|---|
| Odour control system | NO AGM | AGM (0,7 g/napkin) + Zeolite (1 g/napkin) | AGM (0,7 g/napkin) + Silica(1 g/napkin) |
| Malodor (Index) | 100 | 75 | 55 |
| Malodour unpleasantness (MU) | −4.3B | −3.2B | −2.3A |
| % Malador reduction | 0 | 25% | 45% |

What is claimed is:

1. An absorbent article comprising a liquid permeable topsheet, a backsheet and an absorbent core intermediate said topsheet and said backsheet, characterised in that said absorbent article comprises an odour control system consisting of the combination of silica, or a metal silicate excluding transition metals, having a molecular weight of 136 or more, with absorbent gelling material, the ratio by weight of said silica to said absorbent gelling material being from about 1:5 to about 1:1.

2. An absorbent article according to claim 1, wherein said absorbent article comprises from 0.5 g to 5 g of said odour control system.

3. An absorbent article according to claim 1, wherein said article comprises from 20 $gm^{-2}$ to 150 $gm^{-2}$ absorbent gelling material.

4. An absorbent article according to claim 1 wherein said article comprises from 40 gm-2 to 100 gm-2 silica.

5. An absorbent article according to claim 1 wherein said silica is silica gel having an average particle size of from about 15 to about 200 microns.

6. An absorbent article according to claim 1 wherein said absorbent article is a sanitary napkin or a panty liner.

* * * * *